US009278993B2

(12) United States Patent
Subramanian et al.

(10) Patent No.: US 9,278,993 B2
(45) Date of Patent: Mar. 8, 2016

(54) CELL-TARGETING NANOPARTICLES AND USES THEREOF

(75) Inventors: Tamil Selvan Subramanian, Singapore (SG); Padmanabhan Parasuraman, Singapore (SG); Dominik Janczewski, Singapore (SG); Kishore K. Bhakoo, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 936 days.

(21) Appl. No.: 13/236,567

(22) Filed: Sep. 19, 2011

(65) Prior Publication Data

US 2012/0107800 A1    May 3, 2012

Related U.S. Application Data

(60) Provisional application No. 61/383,749, filed on Sep. 17, 2010.

(51) Int. Cl.
| | |
|---|---|
| *A61K 49/18* | (2006.01) |
| *C07K 5/02* | (2006.01) |
| *A61K 49/00* | (2006.01) |
| *B82Y 30/00* | (2011.01) |
| *G01N 33/58* | (2006.01) |

(52) U.S. Cl.
CPC ........... *C07K 5/0215* (2013.01); *A61K 49/0067* (2013.01); *B82Y 30/00* (2013.01); *G01N 33/587* (2013.01); *C07K 2319/09* (2013.01); *C07K 2319/10* (2013.01); *Y10T 428/2982* (2015.01)

(58) Field of Classification Search
CPC ... C07K 5/0215; A61K 49/0067; B82Y 30/00
USPC ........................................... 514/1.1; 424/400
See application file for complete search history.

(56) References Cited

U.S. PATENT DOCUMENTS

| | | | | |
|---|---|---|---|---|
| 2004/0058457 | A1* | 3/2004 | Huang et al. | 436/524 |
| 2004/0115345 | A1* | 6/2004 | Huang et al. | 427/212 |
| 2005/0176142 | A1 | 8/2005 | Nakorn et al. | |
| 2009/0229968 | A1* | 9/2009 | Takeda et al. | 204/157.15 |
| 2010/0021957 | A1 | 1/2010 | Lin et al. | |
| 2011/0111002 | A1* | 5/2011 | Pop | 424/422 |

FOREIGN PATENT DOCUMENTS

WO    WO 2008/133598 A1    11/2008

OTHER PUBLICATIONS

Stephen A. Adam, et al., "Nuclear Protein Import in Permeabilized Mammalian Cells Requires Soluble Cytoplasmic Factors", The Journal of Cell Biology, vol. 111, pp. 807-816, (Sep. 1990).
IUPAC-IUB Joint Commission on Biochemical Nomenclature (JCBN), "Nomenclature and Symbolism for Amino Acids and Peptides—Recommendations 1983", European Journal of Biochemistry, vol. 138, pp. 9-37, (1984).
Neff Michaud, et al., "Multiple Pathways in Nuclear Transport: The Import of U2 snRNP Occurs by a Novel Kinetic Pathway", The Journal of Cell Biology, vol. 112, No. 2, pp. 215-223, (Jan. 1991).
Colin Dingwall, et al., "The Nucleoplasmin Nuclear Location Sequence is Larger and more Complex than that of SV-40 Large T Antigen", The Journal of Cell Biology, vol. 107, pp. 841-849, (Sep. 1988).
Chi V. Dang, et al., "Identification of the Human c-myc Protein Nuclear Translocation Signal", Molecular and Cellular Biology, vol. 8, No. 10, pp. 4048-4054, (Oct. 1988).
Daniel Chelsky, et al., "Sequence Requirements for Synthetic Peptide-Mediated Translocation to the Nucleus", Molecular and Cellular Biology, vol. 9, No. 6, pp. 2487-2492, (Jun. 1989).
Haruhiko Siomi, et al., "A Nuclear Localization Domain in the hnRNP A1 Protein", The Journal of Cell Biology, vol. 129, No. 3, pp. 551-560, (May 1995).
Dirk Gorlich, et al., "Distinct Functions for the Two Importin Subunits in Nuclear Protein Import", Nature, vol. 377, pp. 246-248, (Sep. 21, 1995).
Richard A. Van Etten, et al., "The Mouse Type IV c-abl Gene Product is a Nuclear Protein, and Activation of Transforming Ability is Associated with Cytoplasmic Localization", Cell, vol. 58, pp. 669-678, (Aug. 25, 1989).
Deborah Greenspan, et al., "Two Nuclear Location Signals in the Influenza Virus NS1 Nonstructural Protein", Journal of Virology, vol. 62, No. 8, pp. 3020-3026, (Aug. 1988).
Ming-Fu Chang, et al., "Nuclear Localization Signals, but not Putative Leucine Zipper Motifs, are Essential for Nuclear Transport of Hepatitis Delta Antigen", Journal of Virology, vol. 66, No. 10, pp. 6019-6027, (Oct. 1992).
Thomas Zurcher, et al., "Nuclear Localization of Mouse Mx1 Protein is Necessary for Inhibition of Influenza Virus", Journal of Virology, vol. 66, No. 8, pp. 5059-5066, (Aug. 1992).
Valerie Schreiber, et al., "The Human Poly(ADP-ribose) Polymerase Nuclear Localization Signal is a Bipartite Element Functionally Separate from Dna Binding and Catalytic Activity", The EMBO Journal, vol. 11, No. 9, pp. 3263-3269, (1992).
Francoise Cadepond, et al., "Hormonal Regulation of the Nuclear Localization Signals of the Human Glucocorticosteroid Receptor", Experimental Cell Research, vol. 201, pp. 99-108, (1992).
Margus Pooga, et al., "Cell Penetration by Transportan", The FASEB Journal, vol. 12, No. 1, pp. 67-77, (1998).

(Continued)

*Primary Examiner* — David Lukton
(74) *Attorney, Agent, or Firm* — Blakely, Sokoloff, Taylor & Zafman LLP (57) ABSTRACT

The invention generally refers to a cell-targeting nanoparticle, wherein the cell-targeting nanoparticle is directly conjugated to at least one cysteine-containing peptide, wherein the cysteine-containing peptide is selected from the group consisting of glutathione (GSM, a GSH-containing peptide, and a peptide comprising a nuclear localization signal (NLS) sequence and a transporter sequence, and methods of using the cell-targeting nanoparticle.

29 Claims, 3 Drawing Sheets

(56) References Cited

OTHER PUBLICATIONS

Johannes Oehlke, et al., "Cellular Uptake of an α-helical Amphipathic Model Peptide with the Potential to Deliver Polar Compounds into the Cell Interior Non-Endocytically", Biochimica et Biophysica Acta, vol. 1414, pp. 127-139, (1998).
Maria Lindgren, et al., "Cell-Penetrating Peptides", Trends in Pharmacological Sciences, vol. 21, pp. 99- 103, (Mar. 2000).
Mariola Fotin-Mieczek, et al., "Cationic Cell-Penetrating Peptides Interfere with TNF Signalling by Induction of TNF Receptor Internalization", Journal of Cell Science, vol. 118, No. 15, pp. 3339-3351, (2005).
Leena N. Patel, et al., "Cell Penetrating Peptides: Intracellular Pathways and Pharmaceutical Perspectives", Pharmaceutical Research, vol. 24, No. 11, pp. 1977-1992, (Nov. 2007).
Romanico B. G. Arrighi, et al., "Cell-Penetrating Peptide TP10 Shows Broad-Spectrum Activity against both *Plasmodium falciparum* and *Trypanosoma brucei brucei*", Antimicrobial Agents and Chemotherapy, vol. 52, No. 9, pp. 3414-3417, (Sep. 2008).
Anna Elmquist, et al., "Structure-Activity Relationship Study of the Cell-Penetrating Peptide pVEC", Biochimica et Biophysica Acta, vol. 1758, pp. 721-729, (2006).
James A. Thomson, et al., "Embryonic Stem Cell Lines Derived from Human Blastocysts", Science, vol. 282, pp. 1145-1147, (Nov. 6, 1998).
Chad A. Cowan, et al., "Derivation of Embryonic Stem-Cell Lines from Human Blastocysts", The New England Journal of Medicine, vol. 350, No. 13, pp. 1353-1356, (Mar. 25, 2004).
Charlotte A. Collins, et al., "Stem Cell Function, Self-Renewal, and Behavioral Heterogeneity of Cells from the Adult Muscle Satellite Cell Niche", Cell, vol. 122, pp. 289-301, (Jul. 29, 2005).
Thomas A. Rando, "The Adult Muscle Stem Cell Comes of Age", Nature Medicine, vol. 11, No. 8, pp. 829- 831, (Aug. 2005).
Wen-Lin Li, et al., "Isolation and Characterization of Bipotent Liver Progenitor Cells from Adult Mouse", Stem Cells, Stem Cells, vol. 24, pp. 322-332, (2006).
Tuo Li, et al., "Preparation of $Ag/SiO_2$ Nanosize Composites by a Reverse Micelle and Sol-Gel Technique", Langmuir, vol. 15, No. 13, pp. 4328-4334, (1999).
Dongbai Zhang, et al., "Formation of Crystalline Nanosized Titania in Reverse Micelles at Room Temperature", Journal of Materials Chemistry, vol. 12, pp. 3677-3680, (2002).

The National Institutes of Health, "NIH Human Embryonic Stem Cell Registry Under Former President Bush (Aug. 9, 2001-Mar. 9, 2009)", retrieved from: http://stemcells.nih.gov/research/registry/eligibilitycriteria, 1 pg., (Aug. 9, 2001).
Gopal Iyer, et al., "Peptide Coated Quantum Dots for Biological Applications", IEEE Transactions on Nanobioscience, vol. 5, No. 4, pp. 231-238, (Dec. 2006).
Fanqing Chen, et al., "Fluorescent CdSe/ZnS Nanocrystal-Peptide Conjugates for Long-term, Nontoxic Imaging and Nuclear Targeting in Living Cells", Nano Letters, vol. 4, No. 10, pp. 1827-1832, (2004).
Gang Huang, et al., "A Novel Strategy for Surface Modification of Superparamagnetic Iron Oxide Nanoparticles for Lung Cancer Imaging", Journal of Materials Chemistry, vol. 19, pp. 6367-6372, (2009).
Chenjie Xu, et al., "Monodisperse Magnetite Nanoparticles Coupled with Nuclear Localization Signal Peptide for Cell-Nucleus Targeting", Chem. Asian J., vol. 3, No. 3, pp. 548-552, (Mar. 7, 2008).
Nikhil R. Jana, et al., "Cysteine-Functionalized Polyaspartic Acid: A Polymer for Coating and Bioconjugation of Nanoparticles and Quantum Dots", Langmuir, vol. 26, No. 9, pp. 6503-6507, (2010).
E. Atherton, et al., "Solid Phase Peptide Synthesis: A Practical Approach (The Practical Approach Series)," IRL Press at Oxford University Press, pgs, Title page, v-ix, and 1-105 (Nov. 16, 1989).
Search Report issued by the Intellectual Property Office of Singapore (IPOS) for corresponding Singapore Patent Application No. 201308664, 3 pp., (Mar. 17, 2015).
Written Opinion issued by the Intellectual Property Office of Singapore (IPOS) for corresponding Singapore Patent Application No. 201308664, 5 pp., (Mar. 20, 2015).
Adegboyega K. Oyelere, et al., "Peptide-Conjugated Gold Nanorods for Nuclear Targeting", Bioconjugate Chem., vol. 18, No. 5, pp. 1490-1497, (2007).
Wei Xie, et al., "Nuclear Targeted Nanoprobe for Single Living Cell Detection by Surface-Enhanced Raman Scattering", Bioconjugate Chem., vol. 20, No. 4, pp. 768-773, (2009).
Deendayal Mandal, et al., "Cellular Uptake of Gold Nanoparticles Directly Cross-Linked with Carrier Peptides by Osteosarcoma Cells", J. Mater. Sci.: Mater. Med., vol. 20, No. 1, pp. 347-350, (2009).
Philippe Collas, et al., "The Nuclear Localization Sequence of the SV40 T Antigen Promotes Transgene Uptake and Expression in Zebrafish Embryo Nuclei", Transgenic Research, vol. 5, No. 6, pp. 451-458, (1996).

\* cited by examiner

SEQUENCE LISTING

```
<160> NUMBER OF SEQ ID NOS: 22

<210> SEQ ID NO 1
<211> LENGTH: 12
<212> TYPE: PRT
<213> ORGANISM: artificial
<220> FEATURE:
<223> OTHER INFORMATION: Designed peptide based on SV40 NLS
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 1

Cys Xaa Xaa Xaa Pro Lys Lys Lys Arg Lys Val Xaa
1               5                   10

<210> SEQ ID NO 2
<211> LENGTH: 12
<212> TYPE: PRT
<213> ORGANISM: artificial
<220> FEATURE:
<223> OTHER INFORMATION: Designed peptide based on SV40 NLS
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 2

Cys Gly Xaa Xaa Pro Lys Lys Lys Arg Lys Val Xaa
1               5                   10
```

-continued

```
<210> SEQ ID NO 3
<211> LENGTH: 12
<212> TYPE: PRT
<213> ORGANISM: artificial
<220> FEATURE:
<223> OTHER INFORMATION: Designed peptide based on SV40 NLS
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 3

Cys Gly Cys Xaa Pro Lys Lys Lys Arg Lys Val Xaa
1               5                   10

<210> SEQ ID NO 4
<211> LENGTH: 12
<212> TYPE: PRT
<213> ORGANISM: artificial
<220> FEATURE:
<223> OTHER INFORMATION: Designed peptide based on SV40 NLS
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 4

Cys Gly Cys Xaa Pro Lys Lys Lys Arg Lys Val Xaa
1               5                   10

<210> SEQ ID NO 5
<211> LENGTH: 12
<212> TYPE: PRT
<213> ORGANISM: artificial
<220> FEATURE:
<223> OTHER INFORMATION: Designed peptide based on SV40 NLS

<400> SEQUENCE: 5

Cys Gly Cys Gly Pro Lys Lys Lys Arg Lys Val Gly
1               5                   10

<210> SEQ ID NO 6
<211> LENGTH: 27
<212> TYPE: PRT
<213> ORGANISM: artificial
<220> FEATURE:
<223> OTHER INFORMATION: transporter peptide sequence

<400> SEQUENCE: 6

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 7
<211> LENGTH: 7
<212> TYPE: PRT
<213> ORGANISM: artificial
<220> FEATURE:
<223> OTHER INFORMATION: SV40 NLS
```

```
<400> SEQUENCE: 7

Pro Lys Lys Lys Arg Lys Val
1               5

<210> SEQ ID NO 8
<211> LENGTH: 16
<212> TYPE: PRT
<213> ORGANISM: artificial
<220> FEATURE:
<223> OTHER INFORMATION: nucleoplasmin NLS

<400> SEQUENCE: 8

Lys Arg Pro Ala Ala Thr Lys Lys Ala Gly Gln Ala Lys Lys Lys Lys
1               5                   10                  15

<210> SEQ ID NO 9
<211> LENGTH: 9
<212> TYPE: PRT
<213> ORGANISM: artificial
<220> FEATURE:
<223> OTHER INFORMATION: c-myc NLS

<400> SEQUENCE: 9

Pro Ala Ala Lys Arg Val Lys Leu Asp
1               5

<210> SEQ ID NO 10
<211> LENGTH: 11
<212> TYPE: PRT
<213> ORGANISM: artificial
<220> FEATURE:
<223> OTHER INFORMATION: c-myc NLS

<400> SEQUENCE: 10

Arg Gln Arg Arg Asn Glu Leu Lys Arg Ser Pro
1               5                   10

<210> SEQ ID NO 11
<211> LENGTH: 38
<212> TYPE: PRT
<213> ORGANISM: artificial
<220> FEATURE:
<223> OTHER INFORMATION: hRNPA1 M9 NLS

<400> SEQUENCE: 11

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 12
<211> LENGTH: 41
<212> TYPE: PRT
<213> ORGANISM: artificial
<220> FEATURE:
<223> OTHER INFORMATION: IBB domain from importin-alpha
```

```
<400> SEQUENCE: 12

Arg Met Arg Lys Phe Lys Asn Lys Gly Lys Asp Thr Ala Glu Leu Arg
1               5                   10                  15
Arg Arg Arg Val Glu Val Ser Val Glu Leu Arg Lys Ala Lys Lys Asp
            20                  25                  30
Glu Gln Ile Leu Lys Arg Arg Asn Val
        35                  40

<210> SEQ ID NO 13
<211> LENGTH: 8
<212> TYPE: PRT
<213> ORGANISM: artificial
<220> FEATURE:
<223> OTHER INFORMATION: myoma T protein NLS

<400> SEQUENCE: 13

Val Ser Arg Lys Arg Pro Arg Pro
1               5

<210> SEQ ID NO 14
<211> LENGTH: 8
<212> TYPE: PRT
<213> ORGANISM: artificial
<220> FEATURE:
<223> OTHER INFORMATION: myoma T protein NLS

<400> SEQUENCE: 14

Pro Pro Lys Lys Ala Arg Glu Asp
1               5

<210> SEQ ID NO 15
<211> LENGTH: 8
<212> TYPE: PRT
<213> ORGANISM: artificial
<220> FEATURE:
<223> OTHER INFORMATION: human p53

<400> SEQUENCE: 15

Pro Gln Pro Lys Lys Lys Pro Leu
1               5

<210> SEQ ID NO 16
<211> LENGTH: 12
<212> TYPE: PRT
<213> ORGANISM: artificial
<220> FEATURE:
<223> OTHER INFORMATION: mouse c-abl IV NLS

<400> SEQUENCE: 16

Ser Ala Leu Ile Lys Lys Lys Lys Lys Met Ala Pro
1               5                   10

<210> SEQ ID NO 17
<211> LENGTH: 5
<212> TYPE: PRT
<213> ORGANISM: artificial
<220> FEATURE:
<223> OTHER INFORMATION: influenza virus NS1 NLS

<400> SEQUENCE: 17

Asp Arg Leu Arg Arg
1               5
```

```
<210> SEQ ID NO 18
<211> LENGTH: 7
<212> TYPE: PRT
<213> ORGANISM: artificial
<220> FEATURE:
<223> OTHER INFORMATION: influenza virus NS1 NLS

<400> SEQUENCE: 18

Pro Lys Gln Lys Lys Arg Lys
1               5

<210> SEQ ID NO 19
<211> LENGTH: 10
<212> TYPE: PRT
<213> ORGANISM: artificial
<220> FEATURE:
<223> OTHER INFORMATION: Hepatitis virus delta antigen

<400> SEQUENCE: 19

Arg Lys Leu Lys Lys Lys Ile Lys Lys Leu
1               5                   10

<210> SEQ ID NO 20
<211> LENGTH: 10
<212> TYPE: PRT
<213> ORGANISM: artificial
<220> FEATURE:
<223> OTHER INFORMATION: mouse Mx1 protein

<400> SEQUENCE: 20

Arg Glu Lys Lys Lys Phe Leu Lys Arg Arg
1               5                   10

<210> SEQ ID NO 21
<211> LENGTH: 20
<212> TYPE: PRT
<213> ORGANISM: artificial
<220> FEATURE:
<223> OTHER INFORMATION: human poly(ADP-ribose) polymerase NLS

<400> SEQUENCE: 21

Lys Arg Lys Gly Asp Glu Val Asp Gly Val Asp Glu Val Ala Lys Lys
1               5                   10                  15

Lys Ser Lys Lys
            20

<210> SEQ ID NO 22
<211> LENGTH: 17
<212> TYPE: PRT
<213> ORGANISM: artificial
<220> FEATURE:
<223> OTHER INFORMATION: steroid hormone receptors (human)
      glucocorticoid

<400> SEQUENCE: 22

Arg Lys Cys Leu Gln Ala Gly Met Asn Leu Glu Ala Arg Lys Thr Lys
1               5                   10                  15

Lys
```

CELL-TARGETING NANOPARTICLES AND USES THEREOF

CROSS-REFERENCE TO RELATED APPLICATION

This application claims the benefit of priority of U.S. provisional application No. 61/383,749 filed Sep. 17, 2010, the contents of it being hereby incorporated by reference in its entirety for all purposes.

SEQUENCE LISTING

This application incorporates by reference the material (Sequence Listing) in the ASCII text file P105781_sequencelisting_ST25.txt, created Sep. 19, 2011, having a file size of 6,226 bytes.

FIELD OF THE INVENTION

The present invention relates generally to cell-targeting nanoparticles, in particularly for targeting of cells.

BACKGROUND OF THE INVENTION

Optical imaging of biological and/or chemical conditions of cells and tissues of a living subject is an area of significant importance. One of the biggest challenges in cell biology is the imaging of living cells. Conventional optical labels such as fluorescent dyes or markers are typically introduced into tissue samples to signal changing biological and/or chemical conditions of tissues. However, these conventional labels have many drawbacks. Conventional labels are generally toxic to living cells and tissues comprised of living cells. Furthermore, conventional labels such as fluorescent dyes or green fluorescent proteins (GFP) generally suffer from short-lived fluorescence because the dyes undergo photo bleaching after minutes of exposure to an excitation light source. Therefore, they are unsuitable for optical imaging that requires extended time period of monitoring. Furthermore, these labels are sensitive to environmental changes such as pH and oxygen concentration. Finally, recombinant GFP fusion proteins are cumbersome to construct, and long-term imaging (more than 3 days for example) with GFP requires the time-consuming process of establishing stable-expressing clones.

Other types of labels such as polymeric, magnetic and metallic particles have been introduced into cells. An alternative technology is the use of inorganic semiconductor nanocrystals, or quantum dots. Quantum dots, such as CdSe/ZnS core/shell nanoparticles, are inorganic fluorophores and generally have a size below 10 nm in diameter. Compared to conventional dyes, they have a much higher photobleaching threshold and negligible photobleaching under biological imaging conditions. Quantum dots can be silanized and, in that form, have reduced phototoxicity and are highly resistant to chemical and metabolic degradation.

Typically, there are three steps before quantum dots (QDs) can be employed for biological applications: 1) synthesis; 2) coating; and 3) bio-conjugation. The as synthesized QDs are generally coated with trioctylphosphine oxide (TOPO), hexadecylamine (HDA) or octadecylamine (ODA) and therefore hydrophobic in nature, and are soluble only in organic solvents.

For the design of water-soluble QDs, different coating methods are available and are accomplished either by exchange of TOPO or through hydrophobic addition reactions. TOPO ligands are often exchanged with thiol-functionalized compounds such as mercaptoacetic acid, dihydrolipoic acid, dithiothreitol, and cysteine containing peptides. The QDs have also been coated with inorganic silica or organic protective polymer layer. The coated particles are then bio-conjugated to peptides, proteins or antibodies for cellular tracking applications.

Silica and polymer coatings significantly increased the overall size to about 20 nm and restricted their use in certain imaging applications as the size of QDs determines the renal clearance of the QDs. QDs of size less 5.5 nm resulted in rapid and efficient urinary excretion and elimination from the animal body.

Additionally, during coating and bio-conjugation, the QDs tend to lose their fluorescence (up to 30-40% from the original quantum yield). The labeling of stem cells is an important area in the context of human regenerative medicine for example. However, in most of the cases, the labeling of stem cells with QDs is non-specific. Even though in vitro and in vivo imaging with QDs has been demonstrated, there remains a need to address the problems that exists in the art especially in relation to cell imaging labels associated with the use of particles such as quantum dots and nanoparticles.

SUMMARY OF TIM INVENTION

In one aspect, there is provided a cell-targeting nanoparticle, wherein the cell-targeting nanoparticle is directly conjugated to at least one cysteine-containing peptide, wherein the cysteine containing peptide is selected from the group consisting of glutathione (GSH), a GSH-containing peptide, and a peptide comprising a nuclear localization signal (NLS) sequence and a transporter sequence.

According to various embodiments, the cell-targeting nanoparticle is for targeting a sub-cellular structure of a cell.

In another aspect, there is provided a method for targeting a cell. The method includes incubating at least one cell-targeting nanoparticle as described herein in a culture containing the cell, under conditions which allow the cell to be targeted by the at least one cell-targeting nanoparticle.

In a further aspect there is provided a kit for the targeting of a cell. The kit includes at least one cell-targeting nanoparticle as described herein.

BRIEF DESCRIPTION OF THE DRAWINGS

The invention will be better understood with reference to the detailed description when considered in conjunction with the non-limiting examples and the accompanying drawings, in which.

DETAILED DESCRIPTION OF TIM INVENTION

The live cell imaging of sub-cellular components of a cell and its visualization constitute increasingly important areas of research. In particular, the nucleus has been a desirable target for visualization since the genomic DNA which carries the genetic information of the cell resides in the nucleus and numerous nuclear proteins actively participate in critical cellular processes such as DNA replication, recombination, RNA transcription, DNA damage and repair, genomic alterations, and cell cycle control. In this context, the present invention is based on the surprising finding that the cell-targeting nanoparticle of the invention is able to specifically target a cell, particularly targeting the cell nucleus and its cytoskeletal structure for example. Furthermore, the cell-targeting nanoparticles of the invention are stable in water with little aggregation over time. Additionally, there was no change in the mean particle size of the cell-targeting nanoparticle before and after conjugation with the cysteine-containing peptide as described herein. Without wishing to be bound by any theory, the specific and efficient transport of the cell-targeting nanoparticle into the nuclei of living cells for example, can greatly enhance the diagnosis of disease genotype, the tracking of oligonucleotide drugs, the understanding of biological processing in the nucleus, and the identification of potential nuclear drug candidates for example.

Thus, the present invention provides a cell-targeting nanoparticle, wherein the cell-targeting nanoparticle is directly conjugated to at least one cysteine-containing peptide. The cysteine-containing peptide can be one of glutathione (GSH), a GSH-containing peptide, or a peptide comprising a nuclear localization signal (NLS) sequence and a transporter sequence.

The term "conjugated" in this context can mean any direct linkage or direct coupling between the cysteine-containing peptide and the cell-targeting nanoparticle, whereby these moieties are held together by a covalent bond or non-covalent interactions, for example, ionic or hydrophobic interaction.

The term "peptide" relates to a molecule containing at least two amino acid residues which are linked to each other by peptide bonds. The term "amino acid residue" as used herein refers to an amino acid either in the D or L form or to an amino acid mimetic that can be incorporated into a polypeptide by an amide bond. The amino acid residues may be naturally occurring amino acids or synthetic amino acids as well as modified amino acids and derivatives of naturally occurring amino acids. Such a peptide can be provided in different ways, e.g., by isolating it from naturally occurring sources, by expressing it from an appropriate recombinant nucleic acid molecule and purifying the resulting product by means and methods well known to the person skilled in the art or by chemical synthesis. The chemical synthesis is preferably but not exclusively carried out on solid phase according to standard procedures ("Boc"- or "Fmoc" chemistry (review: Atherton and Sheppard in: Solid phase peptide synthesis, IRL Oxford, University Press (1989)) using an automated peptide synthesizer. Derivatization steps or peptide cyclization may be carried out in fluid phase after cleavage of the peptide from the solid support.

According to various embodiments, the cell-targeting nanoparticle may be directly conjugated to the cysteine-containing peptide by way of a functional group, for example, a thiol group. The thiol group can for example be present in the cysteine-containing peptide, and can be directly coupled to the nanoparticle. As a non-limiting illustrative example, the thiol group of the cysteine-containing peptide may bind directly to a metal of the cell-targeting nanoparticle for example. In other embodiments, the cell-targeting nanoparticle surface may comprise a functional group such as a thiol group for conjugating to the cysteine-containing peptide. In this context, the direct conjugation between the nanoparticle and the cysteine-containing peptide may, for example occur via a disulphide bond.

The term "nuclear localization signal" and "NLS" sequence as described herein are used interchangeably and refers to an amino acid sequence which is capable of inducing transport of molecules comprising such sequence(s) or linked to such sequences into the nucleus of cells. The NLS can, for example, direct transport of a protein with which it is associated from the cytoplasm of a cell across the nuclear envelope barrier. The NLS is intended to encompass not only the nuclear localization sequence of a particular peptide, but also derivatives thereof that are capable of directing translocation of a cytoplasmic polypeptide across the nuclear envelope barrier. NLSs are capable of directing nuclear translocation of a polypeptide when attached to the N-terminus, the C-terminus, or both the N- and C-termini of the polypeptide. In addition, a polypeptide having an NLS coupled by its N- or C-terminus to amino acid side chains located randomly along the amino acid sequence of the polypeptide may be translocated. Adam et al. (1990) *J. Cell. Biol.* 111:807-813.

According to various embodiments, the NLS sequence can include a sequence selected from the group consisting of SEQ ID NO: 1 (C***PKKKRKV*), SEQ if) NO: 2 (CG**PKKKRKV*), SEQ ID NO: 3 (CGC*PKKKRKV*), SEQ ID NO: 4: (CGC*PKKKRKV*) or SEQ 11) NO: 5 (CGCGPKKKRKVG).

"*" or "Xaa" referred herein can be used interchangeably and can be any kind of amino acid known in the art, for example naturally occurring and non-naturally occurring (synthetic) amino acids. Xaa can for example be a D- or L-alpha amino acid residue. Amino acids known in the art (both naturally occurring and synthetic) which can be used for the peptides and/or modified peptides referred to herein (e.g. also for "*" or "Xaa") can include, but are not limited to 2-aminoadipic acid (Aad), aminobutyric acid (Abu), aminobenzoic acid (Abz), aminocyclohexanoic acid (Ac6c), aminocyclopentanoic acid (Ac5c), aminocyclopropanoic acid (Ac3c), aminodecanoic acid (Adc), aminododecanoic acid (Ado), aminohexanoic acid (Ahx), aminoisobutyric acid (Aib), alanine (Ala), alloisoleucine (AIle), allothreonine (aThr), arninomethylbenzoic acid (Amb), aminomethylcyclohexanoic acid (Amc), 2-amino-2-thiazolidine-4-carboxylic acid, aminononanoic acid, aminooctanoic acid, aminopentanoic acid (Avl), arginine (Arg), asparagine (Asn), aspartic acid (Asp), aminoundecanoic acid, aminovaleric acid, biphenylalanine, benzoylphenylalanine, carnitine, 4-cyano-2-aminobutyric acid, 3-cyano-2-aminopropionic acid, cyclohexylalanine, cyclohexylglycine, citruline (Cit), cysteine (Cys), cystine, 2,4-diaminobutyric acid (A2bu), 2,3-diaminopropionic acid (A2pr), diethylglycine, dihydrotryptophan, diaminobenzoic acid, dipropylglycine, 2,3-diaminopropionic acid, 2,3-didehydroalanine (Dha), (Z)-2,3-didehydroaminobutyric acid (Dnb), erythro-3-hydroxyaspartic acid (HyAsp), 2-aminobutyric acid (Abu), dolaproine (Pap), dolaisoluine (Dil), dolaisovaline (Dov), Hiv, methyl valine (MeVal), 3-amino-6-octyneoic acid (Doy), dolaphenine (Doe), dolahexanoic acid (Dhex) 2-methyl-3-aminoisocaproic acid (Dml, dolamethylleuine), 2-amino-4-phenylisovaleric acid (Dpv, dolaphenvaline), diethylglycine, dihydrotryptophan, gamma-carboxyglutamic acid, glutamine (Gln), glutamic acid (Glu), glycine (Gly), histidine (His), homoarginine, homocysteine (Hey), homophenylalanine, homoserine (Hse), homoserinelactone (Hsl), homotyrosine, hydroxylysine (Hyl), hydroxyproline (Hyp), 2-indolinecarboxylic acid, 2-indanylglycine. isoglutamine (iGIn), isoleucine (Ile), indoleglycine, isonipecotic acid, isovaline (Iva), leucine (Leu), lvsine (Lys), β-mercapto-β,β-cyclopentamethylenepropanoic acid, methionine (Met), methionine S-oxide (Met(O)), muramicacid (Mur), napthylalanine, neuraminicacid (Neu), norleucine (Nle), norvaline (Nva), octahydroindolecarboxylic acid, omithine (Orn), pyridylalanine, penicillamine, pyroglutamic acid, phenylalanine (Phe), $C_\alpha$-Me-L-Phenylalanine, phenylglycine, phosphoserine (Ser(P)), pipecolic acid, 4-phosphomethylphenyialanine, propargylglycine, proline (Pro), putrescine, sarcosine (Sar), serine (Ser) statine (Sta), statine analogs, taurine (Tau), thiazolidinecarboxylic acid, tetahydroisoquinoline-3-carboxylic acid, tent-leucine, threonine (Thr), thyroxine (Thx), tryptophan (Trp), tyrosine (Tyr). 3,5-diiodotyrosine (Tyr($I_2$)). valine (Val) and AEEA. Abbreviations for amino acids, as used herein, are in accordance with the IUPAC guidelines on nomenclature (Nomenclature and Symbolism for Amino Acids and Peptides. *Eur. J. Biochem.* 138: 9-37(1984)).

In various embodiments, the NLS sequence can be derived from the nuclear localization sequence of the SV40 virus large T-antigen, the minimal functional unit of which is the seven amino acid sequence PKKKRKV (SEQ ID NO: 7). In other embodiments, the NLS sequence can be derived from nucleoplasmin, for example the nucleoplasmin bipartite NLS with the sequence KRPAATKKAGQAKKKK (SEQ ID NO: 8) (Michaud and Goldfarb, *J. Cell Biol.* 112 (1991), 215-223; Dingwall C. et al, *The Journal of Cell Biology,* 107, 1988, p. 841-849). Other examples in which the NLS sequence can be derived therefrom can include but are not limited to the c-myc nuclear localization sequence having the amino acid sequence PAAKRVKLD (SEQ ID NO: 9) (bang, C. V. et al, *Molecular Cell Biology,* 1988, 8(10), p 4048-4054) or RQRRNELKRSP (SEQ ID NO: 10) (Chesky et al., *Mol. Cell Biol.* 9 (1989). 2487-2492) and the hRNPA1 M9 nuclear localization sequence having the sequence NQSSNFGPMKGGNFGGRSSGPYGGGGQYFAKPRNQGGY (SEQ ID NO: 11) (Siomi and Dreyfuss, J. Cell Biol. 129 (1995), 551-560). Further examples for nuclear localization sequences are the sequence RMRIZFKNKGKDTAELRRRRVEVSVELRKAKKDEQILKRRNV (SEQ ID NO: 12) of the IBB domain from importin-alpha (Gorlich et al., Nature 377 (1995), 246-248), the sequences VSRKRPRP (SEQ ID NO: 13) and PPKKARED (SEQ ID NO: 14) of the myoma T protein (Chelsky et al., loc. cit.), the sequence POPKKKPL (SEQ ID NO: 15) of human p53 (Chelsky et al., loc. cit.), the sequence SALIKKKKKMAP (SEQ ID NO: 16) of mouse c-abl IV (Van Etten et al., Cell 58 (1989), 669-678), the sequences DRLRR (SEQ ID NO: 17) and PKQKKRK (SEQ ID NO: 18) of the influenza virus NS1 (Greenspan et al., *J. Virol.* 62 (1988), 3020-3026), the sequence RKLKKKIKKL (SEQ ID NO: 19) of the Hepatitis virus delta antigen (Chang et al., *J. Virol.* 66 (1992), 6019-6027) and the sequence REKKKFLKRR (SEQ ID NO: 20) of the mouse Mx1 protein (lurcher et al., *J. Virol.* 66 (1992), 5059-5066). It is also possible to use bipartite nuclear localization sequences such as the sequence KRKGDEVDGVDEVAKKKSKK (SEQ ED NO: 21) of the human poly(ADP-ribose) polymerase (Schreiber et al., *EMBO J.* 11 (1992), 3263-3269) or the sequence RKCLQAGMNLEARKTKK (SEQ ID NO: 22) of the steroid hormone receptors (human) glucocorticoid (Cadepond et al, *Exp. Cell Res.* 201 (1992), 99-108).

The transporter sequence as described herein refers to any peptide sequence that facilitates movement of any attached cargo within a cell or cells (for e.g, facilitate cellular uptake of a cell-targeting nanoparticle as described herein), including facilitating cargo movement across a cell membrane of cell. Non-limiting examples can include a transporter sequence derived from a cell penetrating peptide(s) or a protein transduction domain(s). A "cell penetrating peptide" and "protein transduction domain" can also be used interchangeably and is defined as a carrier peptide that is capable of crossing a biological membrane or a physiological barrier. Cell penetrating peptides are also called cell-permeable peptides or membrane-translocation sequences (MTS). Therefore, cell-penetrating peptides can have the ability to translocate in vitro and/or in vivo the mammalian cell membranes and enter into cells, and directs a conjugated compound of interest, such as the cell-targeting nanoparticle for example, to a desired cellular destination, e.g. into the cytoplasm (cytosol, endoplasmic reticulum, Golgi apparatus, etc.) or the nucleus. Without wishing to be bound by theory, the transporter sequence as described herein can direct or facilitate penetration of the cell-targeting nanoparticle as across a phospholipid, mitochondrial, endosomal or nuclear membrane. The transporter sequence can also direct the cell-targeting nanoparticle from outside the cell through the plasma membrane, and into the cytoplasm or to a desired location within the cell, e.g., the nucleus, the ribosome, the mitochondria, the endoplasmic reticulum, a lysosome, or a peroxisome, to mention only a few. Alternatively or in addition, the transporter sequence can direct the cell-targeting nanoparticle across the blood-brain, trans-mucosal, hernatoretinal, skin, gastrointestinal and/or pulmonary barriers.

In various embodiments, the transport sequence can be a cell penetrating peptide. Such sequence are typically polycationic or amphiphilic sequences rich in amino acids with positively charged side groups, for example, basic amino acids such as histidine, lysine and arginine. Non-limiting suitable examples of cell penetrating peptides that are known in the art can include protein membrane transduction domains which are present in transcription factors, such as the homeodomthn proteins, and viral proteins, such as TAT of HP/-1.

According to various embodiments, the transporter sequence can have a sequence in the length of 10 to 50 amino acid residues; or 10 to 40 amino acid residues; 10 to 30 amino acid residues; 10 to 20 amino acid residues; 20 to 50 amino acid residues; about 45 amino acid residues; about 40 amino acid residues; about 35 amino acid residues; about 30 amino acid residues; about 25 amino acid residues; about 20 amino acid residues; or about 15 amino acid residues.

In certain embodiments, the transporter sequence can comprise a sequence selected from a penetratin, transportan (Pooga. et al, *The FASAB Journal*, vol. 12, 1998, pg 67-77) MAP (Oehlke, J. et al (1998) *Biochem. Biophys. Acta* 1414, 127 139), HIV TAT (Maria Lindgren[a], et al., *Trends in Pharmacological Sciences*, vol. 21, 2000, Pages 99-103), Antp (Mariola F et. al., *Journal of Cell Science,* 118 (15), pg 3339-3351), FHV coat protein (Patel L. N. *Pharmaceutical Research*, 24(11), 2007, page 1977-1992), TP10 (Arrighi et al, *Antimicrobial Agents and Chemotherapy*, 2008, 52(9), p.3414-3417) and pliLC amino acid sequence (Elmquist A. et al, *Biochimica et Biophysica Acta (BBA)-Biomembranes,* 1758(6), p.721-729), to mention only a few. In various embodiments, the transporter sequence can comprise an amino acid sequence as set forth in SEQ ID NO: 6 (GWTLNSAGYLLGKINLKALAALAKKIL).

The term "nanoparticle" as used herein refers to any cell-targeting particle having a size from about 1 to about 50 nm and has the capacity to be directly conjugated to at least one cysteine-containing peptide as described herein. The size of the nanoparticle used in the conjugate of the present invention can vary in any size when desired, so long as the nanoparticle has the capability to target a cell. In some embodiments, the diameter of the nanoparticle as described herein can range in the size from about 1 nm to about 50 nm; about 1 rim to about 45 nm; about 1 nm to about 40 nm; about 1 nm to about 35 nm; about 1 nm to about 30 nm; about 1 nm to about 25 nm; about 1 nm to about 20 nm; about 10 nm to about 50 nm; about 15 nm to about 50 nm; about 20 nm to about 50 nm; about 25 nm to about 50 nm; about 30 nm to about 50 nm; about 1 nm to about 10 nm; about 9 nm; about 8 nm; about 7 nm; about 6 nm; about 5 nm; or about 3 nm.

In some embodiments, the cell-targeting nanoparticle comprises a metal nanoparticle. Suitable metals for use in a metal nanoparticle herein can include, but are not limited to, aluminum, iron, silver, zinc, gold, copper, cobalt, nickel, platinum, manganese, rhodium, ruthenium, palladium, titanium, vanadium, chromium, molybdenum, cadmium, mercury, calcium, zirconium, and iridium, or oxides thereof.

In some embodiments, the cell-targeting nanoparticle can comprise a quantum dot. The term "quantum dot" can be defined as a portion of matter in which one or more electrons or holes (excitons) are confined in three spatial dimensions. Non-limiting examples of a quantum dot can be selected from the group consisting of CdSe, CdS, ZnSe, ZnS, PbS, PbSe, CuS and combinations thereof.

According to various embodiments, the cell-targeting nanoparticle can comprise a magnetic nanoparticle. As used herein, the term "magnetic nanoparticle" is meant to include any nanoparticle which moves in response to being placed in an appropriate magnetic field. This term is meant to also include ferromagnetic, paramagnetic and diamagnetic materials. Non-limiting suitable examples can include, $Fe_2O_3$, $Fe_3O_4$, $Fe_2O_4$, $Fe_xPt_y$, $Co_xPt_y$, $MnFe_xO_y$, $CoFe_xO_y$, $NiFe_xO_y$, $CuFe_xO_y$, $ZaFe_xO_y$, and $CdFe_xO_y$, wherein x and y vary between 1 and 6, depending on the method of synthesis known in the art.

According to various embodiments, the cell-targeting nanoparticle targets a sub-cellular structure of a cell. The sub-cellular structure can be part of an intact cell, which can be part of a multicellular tissue or organ or it can be present together with other cells of the same or different types of in a cell culture. In some embodiments, the sub-cellular structure can be one of organelle, cytoskeleton, genetic material and combinations thereof.

The term "cytoskeleton" refers to a complex network of protein filaments traversing the cell cytoplasm. The cytoskeleton is present in all cells including eukaryotes and prokaryotes. It is not simply a passive feature of the cell that provides structural integrity, but is a dynamic structure that is responsible for whole-cell movement, changes in cell shape, and contraction. Some cytoskeletal fibers may connect to organelles or provide tracks along which organelles and/or small molecules move. In some embodiments, the cytoskeleton can be one of an actin filament, a microtubule, an intermediate filament and combinations thereof.

The term "organelle" refers to a sub-cellular unit defined by the plasma membrane of the cell. The organelle includes, but is not limited to, nucleus, nucleolus, nuclear matrix, nuclear lamina, core filaments, nuclear envelope, nuclearpore complexes, and nuclear membranes. The organelle also includes mitochondrion, endoplasmic reticular, Golgi complexes or Golgi apparatus, lysosomes and vacuoles. The organelle further includes chromosomes, nucleosome, chromatin, centromere, centrosome, centrioles, pericentriolar material, mitotic spindle, spindle pole bodies, contractile rings, kinetochore, proteomes, telomere, plasma membranes, endosomes, perioxomes, phagosomes and ribosome& Each organelle plays a unique role in the growth, metabolism and metastasis of tumor cells, and each contains a collection of specific proteins or enzymes that catalyze the requisite chemical reactions.

The term "genetic material" refers to natural nucleic acids, artificial nucleic acids, non-natural nucleic acid, orthogonal nucleotides, analogs thereof, or combinations thereof. Genetic material can also include analogs of DNA or RNA having modifications to either bases or the backbone. Genetic material also includes the use of peptide nucleic acids (PNA). The term "genetic material" also includes chimeric molecules. The genetic material can include or consist of a nucleic acid of one or more strands of a single and/or double stranded material. Genetic material from a subject is generally numerous strands and genes and can for example, include the entire genome of the subject. Genetic material can comprise or consist of nucleic acids. Exemplary genetic materials include DNA, RNA, mRNA and mlRNA and any combinations thereof.

According to various embodiments, the cell that is targeted by the cell-targeting nanoparticle of the invention can be derived from a mammal or invertebrate species, or in a microorganism. Examples of mammals include, but are not limited to, a rat, a mouse, a dingo, a cow, a pig, a goat, a chimpanzee, a macaque, and a human.

In other embodiments, the cell can be a stem cell. The term "stem cell" as used herein refers to any cell(s) that has the ability to differentiate for indefinite periods of time and to give rise to specialized cells for example, any organ, cell type or tissue type. A stem cell emanates from germinal layers (ectoderm, mesoderm and endoderm. Typical sources of stem cells include embryos, bone marrow, peripheral blood, umbilical cord blood, and placental blood. Stem cells can be pluripotent, meaning that they are capable of generating most tissue on an organism. For example, pluripotent stem cells can give rise to cells of the skin, liver, blood, muscle, bone, and the like. In some embodiments, the stem cell can be a bone marrow stem cell. In other embodiments, the stem cell can be a mesenchymal stem cell. A "mesenchymal stem cell" generally refers to a population of cells derived from embryonic stem cells. Mesenchymal stem cell directly originate from the mesoderm and are either partially differentiated cells or proliferative precursor cells committed to form cells of a mesenchymal tissue (such as bone derived from osteoblast cells), dental tissue, cartilage, tendon, bone marrow stroma, or muscle. Mesenchymal stem cells are included in the term, as are differentiated (post-mitotic) cells and more committed replication-competent cells, such as bone precursor cells=

Any stem cell for example a pluripotent human embryonic stem cell or a respective cell line may be used in the present invention. Means of deriving a population of such cells are well established in the art (cf. e.g. Thomson, J. A. et al. [1998] *Science* 282, 1145-1147 or Cowan, C. A. et al. [2004] *N. Engl. J. Med.* 350, 1353-1356). Furthermore, 71 independent human ESC lines are for example known to exist, of which several cell lines are available for research purposes (see e.g. the NIH Human Embryonic Stem Cell Registry at http://stemcells.nih.gov/research/registry/eligibilityCriteria.asp), such as GE01, GE09, BG01, BG02, TE06 or WA09. Adult stem cells may for instance be isolated from blood from the placenta and umbilical cord left over after birth, or from myofibers, to which they are associated as so called "satellite cells" (Collins, C. A. et al. [2005] *Cell* 122, 289-301, see also Lando, T. A. [2005] *Nature Medicine* 11, 8, 829-831).

Any progenitor cell may also be used according to the invention. Examples of suitable progenitor cells include, but are not limited to, neuronal progenitor cells, endothelial progenitor cell, erythroid progenitor cells, cardiac progenitor cells, oligodendrocyte progenitor cells, retinal progenitor cells, or hematopoietic progenitor cells. Methods of obtaining progenitor cells are well known in the art. As two illustrative examples, a method of obtaining megakaryocyte progenitor cells has been disclosed in US patent application 2005/0176142 and a method of obtaining mouse liver progenitor cell lines has been described by Li et al. ((2005) *Stem Cell Express*, doi:10.1634/stemcells.2005-0108).

Other examples of stem cells that may be used according to the present invention include, but are not limited to, embryonic stem cells, trophoblast stem cells and extraembryonic stem cells. In some embodiments an ESC (embryonic stem cell), such as an ESC of human origin, i.e. a human ESC may thus be used. In other embodiments the cell is a progenitor cell (cf above). In yet other embodiments the cell is a cancer cell. An illustrative example of a cancer cell is teratoma cancer cell, such as for example F9, NTERA2, C3H, TES-1, 1246 (including 1246-3A), SuSa (including SuSa/DXR10 and SKOV-3/D)-(R10), AT805 (including ATDC5), HTST, HGRT, PC (e.g. PCC3/A/1) or GCT27. Two further illustrative example of a cancer cell are a HeLa cell and an MCF-7 cell. In some embodiments the cell is a hybrid cell of a stem cell and a somatic cell.

The cell-targeting nanoparticle of the invention can be formed using reverse-microemulsion techniques known to persons skilled in the art, as described for example, in Li T. et al, *Langmui*, 1999, 15(13), p. 4328-4334; Thong D. J. *Mater, Chem.*, 2002, 12, 3677-3680. A non-limiting example of the present method is described in the present examples.

In various embodiments, there is provided a method for targeting a cell comprising incubating at least one cell-targeting nanoparticle as described herein in a culture containing the cell, under conditions which allow the cell to be targeted by the at least one cell-targeting nanoparticle. In other embodiments, the method can include contacting at least one call-targeting nanoparticle with a cell to be targeted.

In various embodiments, a kit is provided for the targeting of a cell. The kit can include at least one cell-targeting nanoparticle as described herein for targeting a cell. The kit can optionally include instructions for carrying out the method described herein. The kit can further include at least one staining agent to detect the targeted cell.

In various embodiments, there is also provided use of at least one cell-targeting nanoparticle for delivery of a drug into the cell.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations ate considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXAMPLES

Example 1

Glutathione (GSH) Coating of CdSe-ZnS Quantum Dots (ODs)

The glutathione (GSH) coating of quantum dots (QDs) was done in Igepal (0.11 M) reverse micelles in cyclohexane. To the 6 ml of micelles, 100 µl aqueous GSH solution (140 mg/nal of water) was added and stirred for about 5 min until the solution became clear. To deprotonate the carboxyl and thiol groups, either 100 µl TMAH (tetramethyl ammonium hydroxide in 2-propanol/methanol mixture) or 40 µl $NH_4OH$ was added. Finally, TOPO-capped CdSe—ZnS QDs, 100-300 µl (5 mg/ml of chloroform) were added and stirred for 1 h.

The hydrophobic QDs would remain in the oil phase, cyclohexane. The interaction of thiol groups (from GSH) with ZnS carping (from CdSe—ZnS ODs) would occur at the water/oil interface, rendering the hydrophilic surface (—COO—) for the QDs. The GSH-coated QDs (QDs@GSH) in the microemulsion were flocculated by the addition of about 2 mL of ethanol and centrifuged at 6000 rpm for 5 min. The fluorescent pellet was washed with 1:1 volume of cyclohexane and ethanol, and centrifuged one more time. The dried pellet was readily soluble in de-ionized water. The pH of the coated particles in water was about 7.

Example 2

Glutathione (GSH) Coating of $Fe_2O_3$ Nanoparticles

The reverse microemulsion method as described in Example 1 was used to form the GSH-coated magnetic $Fe_2O_3$ particles (MPs@GSH). The octadecylamine (ODA) capped magnetic particles, 100 µl (10 mg/ml, of chloroform) were added in place of QDs. The purified coated particles were soluble in water.

Figure 2:
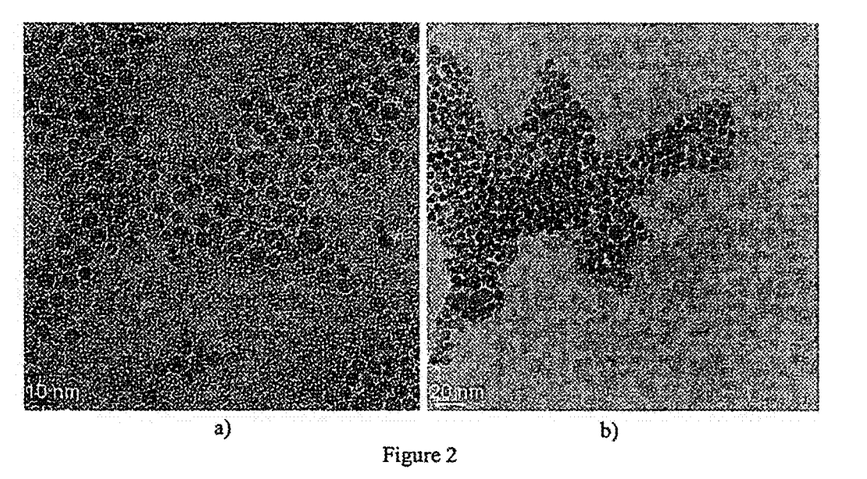
FIG. 2 depicts the transmission electron microscopy (TEM) images of (a) $Fe_2O_3$ magnetic nanoparticles in chloroform; (b) glutathione (GSH)-coated nanoparticles dispersed in water, according to various embodiments.

The MPs@GSH are stable in water with little aggregation over time. The reverse microemulsion technique allows a facile transfer of MPs to water with no aggregation as shown in FIG. 2. Additionally, the peptide coating did not alter the mean particle size. The diameter of the MPs before and after coating is about 6 nm.

Example 3

Cell Labeling of Bone Marrow Stem Cells (BMSCs) UsinG QDs@GSH

The labeling of stem cells was carried out using the following procedure. BMSCs were harvested from femurs and tibias of adult male Wistar rats. Haematopoietic and other non-adherent cells were removed during medium changes. After 10 to 14 days of primary cultivation, the adherent cells were nearly 80% confluent and were dissociated with 0.25% trypsin.

Figure 1:
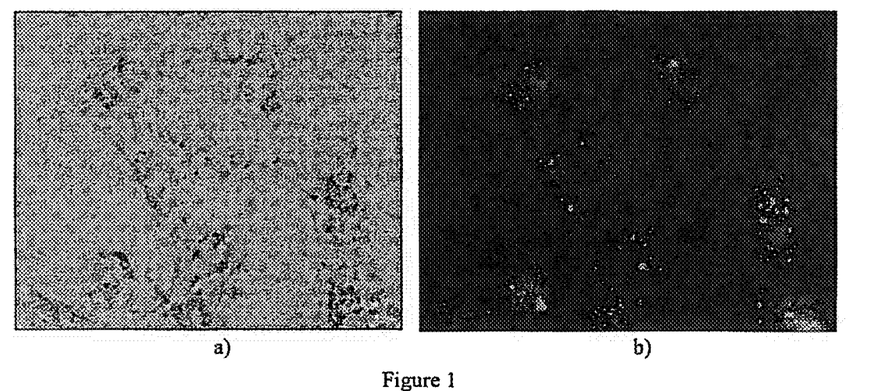
FIG. 1 depicts the transmittance (a) and fluorescence (b) images of bone marrow stem cells (BMSCs) labeled with glutathione coated quantum dot ("QD@GSH") and DAPI fluorescent stain, according to various embodiments. The cell membrane and the nucleus are labeled by QD@GSH particles.

The cells were cultured with different concentrations of green emitting GSH-QDs and stained with a nuclear staining agent, 4',6-diamidino-2-phenylindole (DAN). First, BMSCs were seeded into six well plates on glass cover slips with approximately 50,000 cells. BMSCs were incubated with QDs at different concentrations viz. 0.5, 5, 20, 30, or 50 nM for 5 mM, 30 min, 2 h, 6 h, 12 h or 16 h. After removal of extra cellular QDs with PBS (three times), the cells attached on to the glass slips were counterstained with VECTASHIELD® HardSet™ Mounting Medium. This special formulation contained a counter stain for DNA (DAPI) and was ready to use for fluorescence in-situ hybridization (FISH) or any other procedures requiring fluorescence counterstaining of DNA. After 4 h of mounting, fluorescent microscopic images (Nikon 901 with FL/DIC/Phase) of QD labeled BMSCs were obtained. Green fluorescence indicated the presence of QDs. In addition to GSH-QDs, the cells were also stained by DAN (blue emission), an organic dye specific for staining nuclei. FIG. 1 illustrates the transmittance (left) and fluorescence (right) images of BMSCs labeled with QD@GSH and DAPI. The cell membrane and the nucleus are labeled by the QD@GS11 particles.

Example 4

Peptide Coating of CdSe—ZnS Quantum Dots (ODs)

The reverse microemulsion method as described in Example 1 was used to form the peptide-coated QDs wherein the peptide comprises the following two sequences:

(SV40 NLS) Ac-CGCGPKKKRKVG-Amide
and (TP) Ac-GWTLNSAGYLLGKINLKALAALAKKIL-Amide wherein
C—Cysteine, G—Glycine, P—Proline, K—Lysine, R—Arginine, V—Valine, W—Tryptophan, T—Threonine, L—Leucine, N—Asparagine, S—Serine, A—Alanine, Y—Tyrosine, I—Isoleucine.

Example 5

Labeling Human Methenchymalst Stem Cells (hMSCs) Using Peptide-coated ODs Prepared in Example 4

Figure 3:
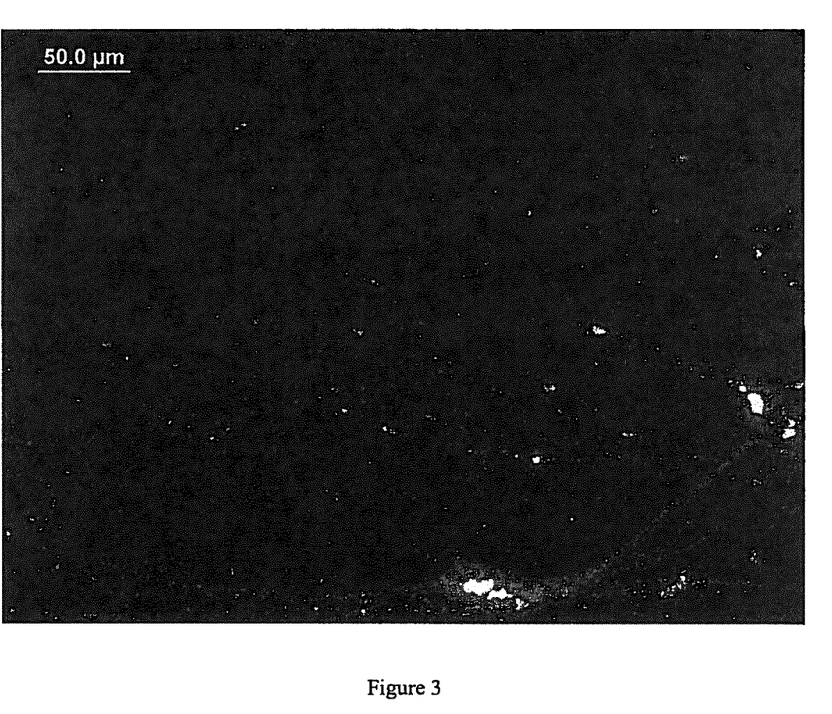
FIG. 3 depicts the nuclear targeting of human mesenchymal stem cells (hMSC) using peptide coated quantum dots wherein the peptide comprising a transporter peptide (TP) fragment and a nuclear localizing signal (NLS) peptide fragment, according to various embodiments.
Figure 4:
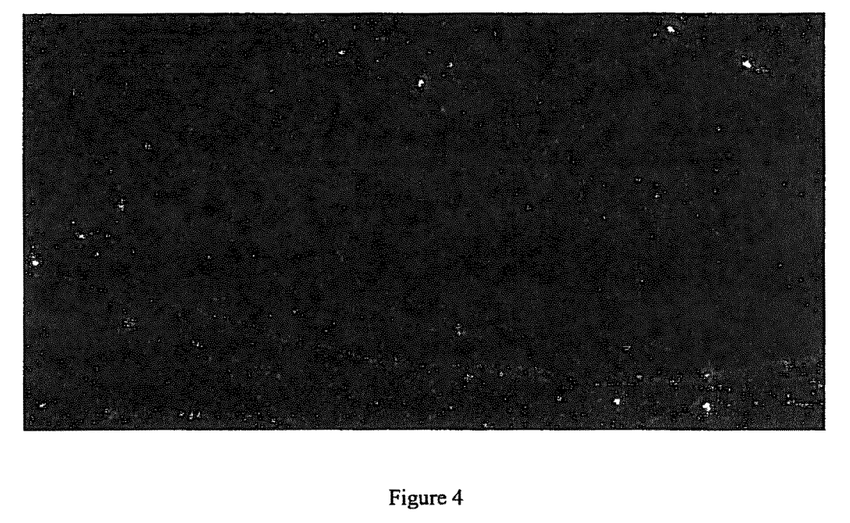
FIG. 4 depicts the targeting of microtubules and filaments of hMSC cells using peptide coated quantum dots wherein the peptide comprising a TP fragment and a NLS peptide fragment, according to various embodiments.

The labeling procedure as described in Example 3 was used, with human mechenchymal stem cells (hMSCs) replacing the BMSCs in example 3. As illustrated in FIG. 3. the peptide-coated ODs targets and labels the nucleus of the hMSCs. FIG. 4 illustrates that the peptide-coated ODs targets and labels the microtubules and actin filaments.

What is claimed is:

1. A cell-targeting nanoparticle, wherein the cell-targeting nanoparticle comprises a quantum dot directly conjugated to at least one cysteine-containing peptide, wherein the cysteine-containing peptide is selected from the group consisting of glutathione (GSH), a GSH-containing peptide, and a peptide comprising a nuclear localization signal (NLS) sequence and a transporter sequence.

2. The cell-targeting nanoparticle of claim 1, wherein the cell-targeting nanoparticle is directly conjugated to the cysteine-containing peptide via a functional group.

3. The cell-targeting nanoparticle of claim 2, wherein the functional group is a thiol group.

4. The cell-targeting nanoparticle of claim 1, wherein the cell-targeting nanoparticle surface comprises at least one functional group for conjugating to the at least one cysteine-containing peptide.

5. The cell-targeting nanoparticle of claim 4, wherein the functional group is a thiol group.

6. The cell-targeting nanoparticle of claim 1, wherein the NLS sequence is derived from SV40 Large T antigen or nucleoplasmin.

7. The cell-targeting nanoparticle of claim 6, wherein the NLS sequence comprises a sequence selected from the group consisting of SEQ ID NO: 1 (C***PKKKRKV*), SEQ ID NO: 2 (CG**PKKKRKV*), SEQ ID NO: 3 (CGC*PKKKRKV*), SEQ ID NO: 4: (CGC*PKKKRKV*) or SEQ ID NO: 5 (CGCGPKKKRKVG).

8. The cell-targeting nanoparticle of claim 1, wherein the transporter sequence comprises a sequence of 10 to 50 amino acid residues or 10 to 30 amino acid residues in length.

9. The cell-targeting nanoparticle of claim 1, wherein the transporter sequence comprises the amino acid sequence as set forth in SEQ ID NO: 6 (GWTLNSAGYLLGKINLKA-LAALAKKIL).

10. The cell-targeting nanoparticle of claim 1, wherein the diameter of the nanoparticle is in the range of about 1 nm to about 50 nm.

11. The cell-targeting nanoparticle of claim 1, wherein the quantum dot is selected from the group consisting of CdSe, CdS, ZnSe, ZnS, PbS, PbSe, CuS and combinations thereof.

12. The cell-targeting nanoparticle of claim 1, wherein the nanoparticle is for targeting a sub-cellular structure of a cell.

13. The cell-targeting nanoparticle of claim 12, wherein the sub-cellular structure is selected from the group consisting of organelle, cytoskeleton and genetic material.

14. The cell-targeting nanoparticle of claim 13, wherein the organelle is selected from the group consisting of nucleus, nucleolus, ribosome, vesicle, rough endoplasmic reticulum, Golgi apparatus, smooth endoplasmic reticulum, mitochondria, vacuole, cytosol, lysosome and centriole.

15. The cell-targeting nanoparticle of claim 13, wherein the cytoskeleton is selected from the group consisting of an actin filament, a microtubule, and an intermediate filament.

16. The cell-targeting nanoparticle of claim 13, wherein the genetic material is deoxyribonucleic acid (DNA) or ribonucleic acid (RNA).

17. The cell-targeting nanoparticle of claim 12, wherein the cell is derived from a human.

18. The cell-targeting nanoparticle of claim 12, wherein the cell is a stem cell.

19. The cell-targeting nanoparticle of claim 18, wherein the stem cell is a bone marrow stem cell or a mesenchymal stem cell.

20. A method for targeting a cell comprising incubating at least one cell-targeting nanoparticle in a culture containing the cell, under conditions which allow the cell to be targeted by the at least one cell-targeting nanoparticle, wherein the cell-targeting nanoparticle comprises a quantum dot directly conjugated to at least one cysteine-containing peptide, wherein the cysteine-containing peptide is selected from the group consisting of glutathione (GSH), a GSH-containing peptide, and a peptide comprising a nuclear localization signal (NLS) sequence and a transporter sequence.

21. The method of claim 20, wherein the sub-cellular structure of the cell is targeted by the cell-targeting nanoparticle.

22. The method of claim 21, wherein the sub-cellular structure is selected from the group consisting of organelle, cytoskeleton and genetic material.

23. The method of claim 22, wherein the organelle is selected from the group consisting of nucleus, nucleolus, ribosome, vesicle, rough endoplasmic reticulum, Golgi apparatus, smooth endoplasmic reticulum, mitochondria, vacuole, cytosol, lysosome and centriole.

24. The method of claim 22, wherein the cytoskeleton is selected from the group consisting of an actin filament, a microtubule, and an intermediate filament.

25. The method of claim 22, wherein the genetic material is deoxyribonucleic acid (DNA) or ribonucleic acid (RNA).

26. The method of claim 20, wherein the cell is derived from a human.

27. The method of claim 20, wherein the cell is a stem cell.

28. The method of claim 27, wherein the stem cell is a bone marrow stem cell or a mesenchymal stem cell.

29. The method of claim 20, wherein the method is carried out using fluorescence spectroscopy or magnetic resonance imaging.

* * * * *